United States Patent [19]

Ford et al.

[11] Patent Number: 5,616,300
[45] Date of Patent: Apr. 1, 1997

[54] PRIMING AND INJECTION VALVE FOR ANALYTICAL INSTRUMENTS

[75] Inventors: Douglas W. Ford, West Linn; Robert W. Todd; Quinn E. Trammell, both of Gresham; Dennis A. Higley, Oregon City, all of Oreg.

[73] Assignee: Optimize Technologies, Inc., Portland, Oreg.

[21] Appl. No.: 448,669

[22] Filed: May 24, 1995

Related U.S. Application Data

[63] Continuation of Ser. No. 69,713, Jun. 1, 1993, abandoned.

[51] Int. Cl.⁶ .................................................. G01N 35/10
[52] U.S. Cl. .......................... 422/103; 422/63; 422/70; 436/174; 436/180; 251/352; 251/339; 251/304
[58] Field of Search .......................... 422/99, 63, 100, 422/103, 104; 436/54, 174, 180; 251/352, 339, 304

[56] References Cited

U.S. PATENT DOCUMENTS

| | | |
|---|---|---|
| 359,939 | 3/1887 | Palmer . |
| 397,904 | 2/1889 | Folmer . |
| 1,914,736 | 6/1933 | Coutu . |
| 3,186,437 | 6/1965 | Buono .................................. 137/625.42 |
| 3,599,681 | 8/1971 | Hall ............................................ 141/18 |
| 3,630,371 | 12/1971 | Hrdina ..................................... 210/198 |
| 3,926,187 | 12/1975 | Iglesias ................................... 128/232 |
| 4,168,235 | 9/1979 | Guillemin et al. ...................... 210/198 |
| 4,529,167 | 7/1985 | Harrison et al. ........................ 251/144 |
| 4,541,452 | 9/1985 | Paradis ..................................... 137/209 |
| 4,662,396 | 5/1987 | Avnon .................................... 137/616.7 |
| 4,819,684 | 4/1989 | Zaugg et al. ............................. 137/112 |
| 4,994,180 | 2/1991 | Sims et al. ............................. 210/198.2 |

*Primary Examiner*—Long V. Le
*Attorney, Agent, or Firm*—Christensen, O'Connor, Johnson & Kindness PLLC

[57] ABSTRACT

A valve (10) is used to introduce fluid from a syringe (22) into the inlet (88) of the pump of an HPLC instrument (12). The valve includes a valve body (14) that is connected to the HPLC instrument for fluid flow communication with the instrument inlet. A valve rotor (16) is rotatably engaged with the valve body. A collar fitting (18) included on the valve rotor is connectable to the syringe. The syringe acts as a valve lever, and is displaceable to rotate the valve rotor about an axis of rotation (32) between an "off" position, in which fluid flow between the syringe and the HPLC instrument inlet is prevented, and an "on" position, in which fluid flow between the syringe and the HPLC instrument inlet is permitted. The valve enables one-handed priming operation.

13 Claims, 2 Drawing Sheets

5,616,300

1

PRIMING AND INJECTION VALVE FOR ANALYTICAL INSTRUMENTS

This application is a continuation application based on prior application Ser. No. 08/069,713, filed on Jun. 1, 1993, now abandoned.

FIELD OF THE INVENTION

The present invention relates to instruments for chemical analysis, and more particularly for valves used in introducing fluids to analytical instruments.

BACKGROUND OF THE INVENTION

Many conventional high performance liquid chromatography (HPLC) instruments include a piston operated pump that must be primed with carrier solvent prior to usage. Conventional equipment and techniques involve a cumbersome set of steps to prime an HPLC pump. A piece of flexible tubing, such as teflon tubing, is typically connected onto the fitting on the distal end of a syringe, with the other end of the tubing being connected to a priming valve that is assembled in line with the pump inlet. A technician supports the connected syringe with one hand, and reaches with the other hand to turn a handle of the priming valve mechanism, thereby opening the valve. Air is then withdrawn into the syringe from the priming valve. The piston of the syringe is then depressed to inject liquid through the open priming valve into the pump, after which the handle of the priming valve is turned to close the valve. Because the priming valve is separate from the syringe, the technician must use both hands. Great care is also required to avoid introduction of air or other contaminants into the system.

SUMMARY OF THE INVENTION

The present invention provides a valve for use in controlling fluid flow between the inlet of an analytical instrument and a fluid reservoir, such as a syringe. The valve includes a valve body that is connectable to the instrument for fluid flow communication with the instrument inlet. The valve further includes a valve rotor that is rotatably engaged with the valve body for rotation about an axis of rotation. A fitting included on the valve rotor is connectable to the syringe, whereby the syringe is displaceable to rotate the valve rotor about its axis of rotation between an "off" position, in which fluid flow between the syringe and the instrument inlet is prevented, and an "on" position, in which the syringe is in fluid flow communication with the instrument inlet.

In a preferred embodiment, the valve rotor includes a radially disposed collar fitting that is engageable with the fitting on the distal end of a syringe, such that the syringe acts as a lever handle for rotation of the valve rotor. The valve of the present invention can be used for one-handed priming of HPLC equipment. The valve is constructed such that the collar fitting and connected syringe depend downwardly from horizontal when the valve rotor is in the "off" position. When the valve rotor is rotated to the "on" position by displacing the syringe, the collar fitting and syringe are disposed in an upwardly depending disposition.

The procedure for priming an HPLC pump using the valve of the present invention thus simply consists of mating the charged syringe to the priming valve, rotating the valve to the "on" position using the syringe as a handle, withdrawing air from the priming valve into the syringe, and then injecting liquid into the priming valve and instrument inlet

2 by depressing the syringe plunger, with air being retained within the syringe. The valve is then rotated to the "off" position, again using the syringe as a lever handle.

The valve of the present invention can also be used to inject analyte samples into an HPLC instrument in similar fashion. Likewise, the valve can be used for introducing liquid into other types of chemical analytical instruments, such as mass spectrometers and capillary electrophoresis devices. Additionally, the valve of the present invention can be used for withdrawing fluid from fluid reservoirs into a syringe, without introducing impurities into the fluid reservoir.

BRIEF DESCRIPTION OF THE DRAWINGS

The present invention will be better understood by reference to the following detailed description, when taken in conjunction with the accompanying drawings, wherein.

DETAILED DESCRIPTION OF THE PREFERRED EMBODIMENT

Figure 1:
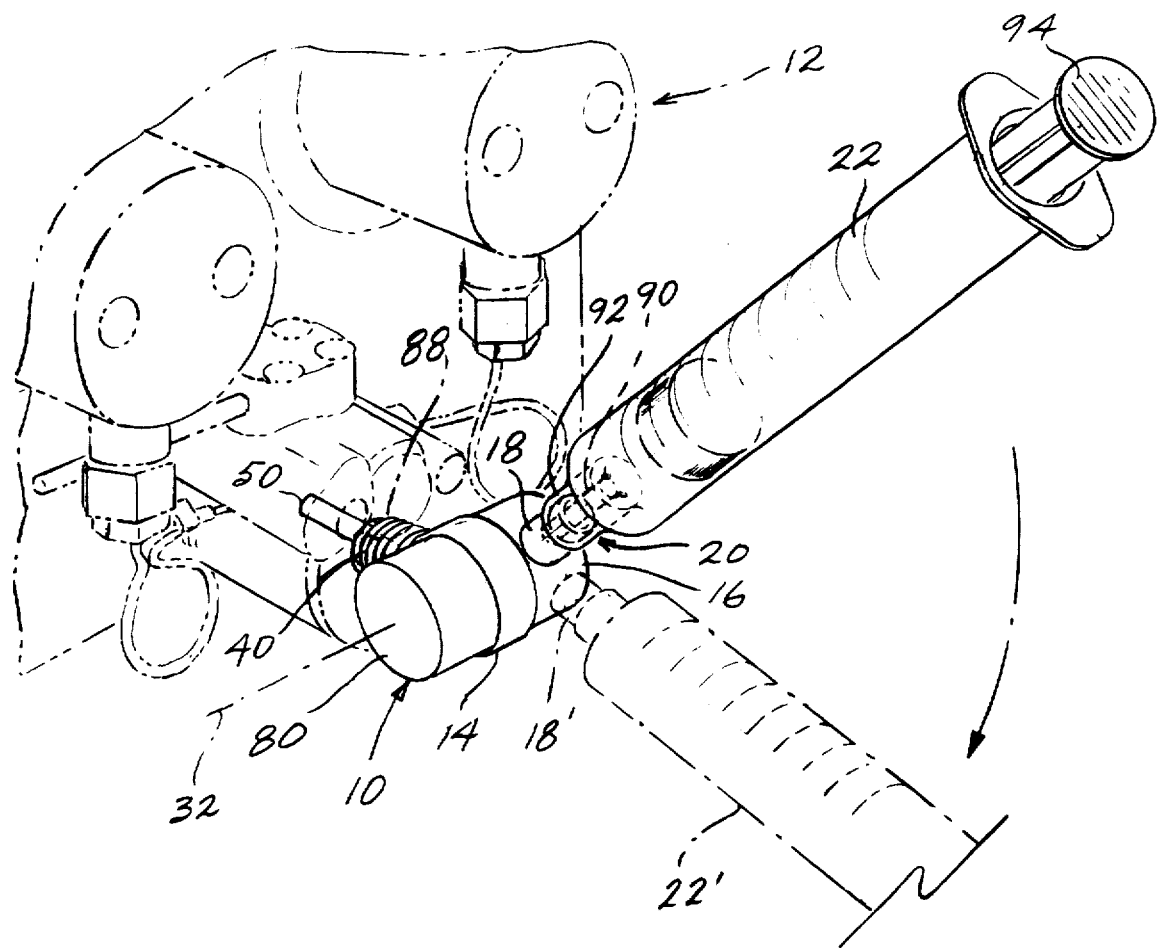
FIG. 1 is a pictorial view of a valve constructed in accordance with the present invention connected to the pump of a HPLC unit (shown partially, in phantom) and a syringe (in phantom), with the valve being shown in the "on" position, and the valve and syringe also being shown in phantom rotated to the "off" position.

A valve 10 constructed in accordance with the present invention is shown in FIG. 1 connected to an HPLC instrument 12. The valve 10 includes a stationary valve body 14 and a valve rotor 16. A collar fitting 18 on the valve rotor 16 is connected to the distal end fitting 20 of a syringe 22. The syringe 22 acts a lever handle to rotate the valve rotor 16 between an "on" position, as shown, and an "off" position, as indicated in phantom by collar fitting 18' and syringe 22'.

The valve 10 is shown installed for use as a priming valve for an HPLC instrument. The installation and method of use of the preferred embodiment of the valve 10 will be described for this application. However, it should be readily understood that the valve 10 may be used for other purposes as well. For example, in addition to use for priming the pump on an HPLC instrument, the valve 10 can be used to inject a sample into a carrier fluid stream flowing into the HPLC instrument. For an injection application, the valve 10 can be threaded into a junction block through which the carrier fluid stream is flowing. The valve 10 can similarly be used for introduction of fluids into other types of chemical analytical instruments, such as mass spectrometers. In addition, the valve 10 can be used to introduce or withdraw fluid from a fluid reservoir, such as withdrawing a syringe sample of fluid from a jar of analyte while avoiding the introduction of any impurities or contaminants into the jar.

Figure 2:
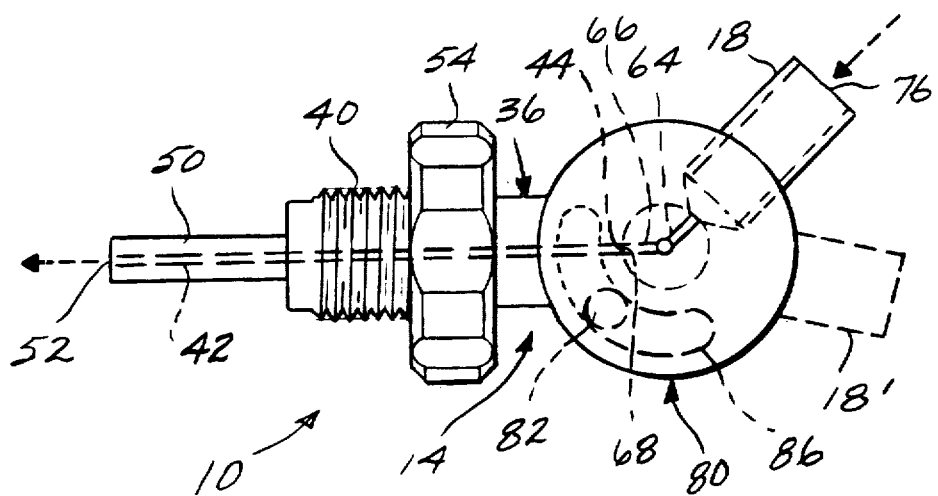
FIG. 2 provides a leer side elevation view of the valve shown in FIG. 1, configured in the "on" position.
Figure 3:
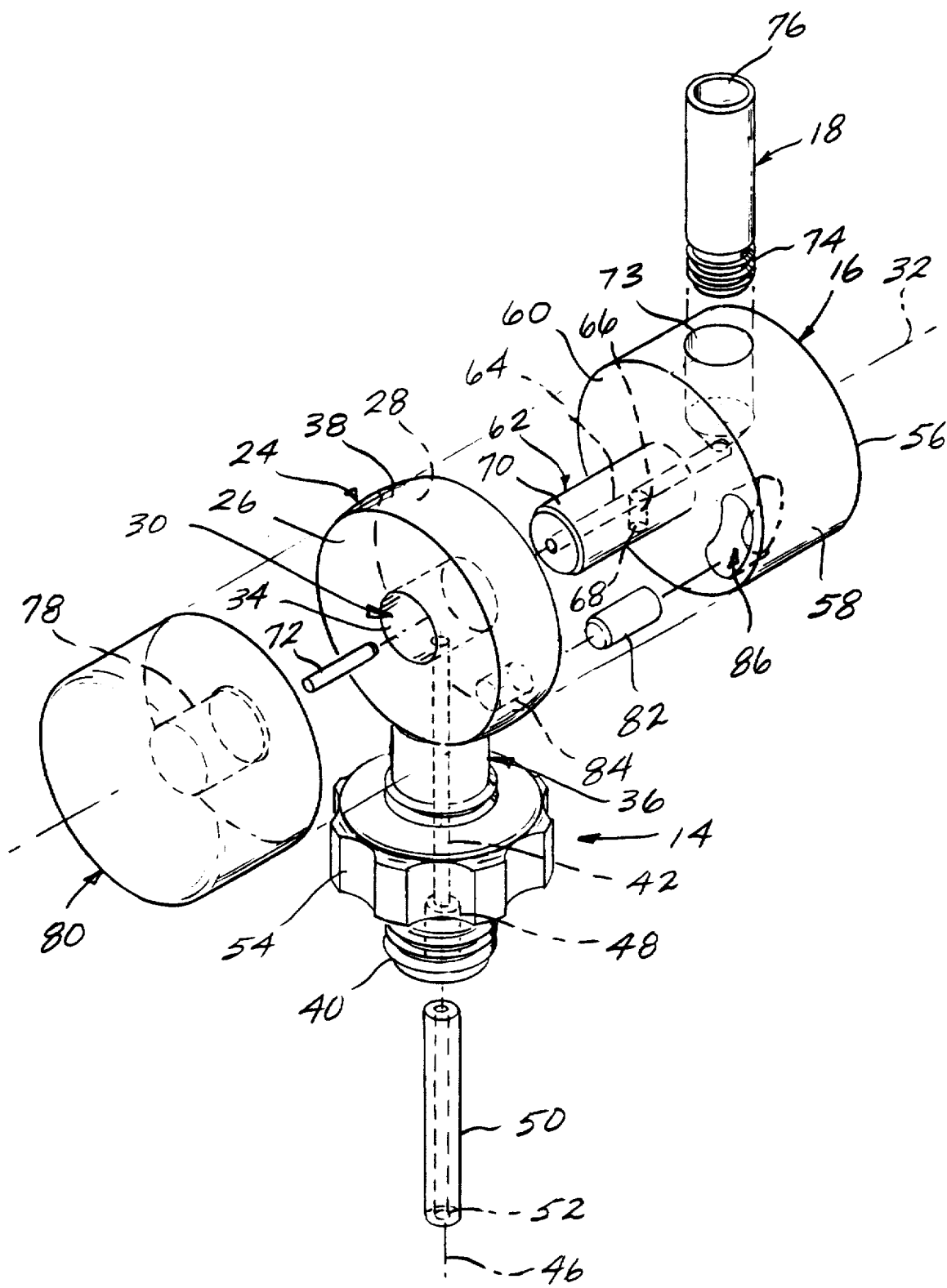
FIG. 3 shows an exploded isometric view of the valve of FIG. 1.

Referring to FIGS. 2 and 3, the valve body 14 includes a disk portion 24 defining first and second parallel, circular bearing surfaces 26 and 28. A central aperture 30 passes from the first surface 26 to the second surface 28. The central aperture 30 is centered on a longitudinal rotational axis 32, which is oriented orthogonally to the first and second bearing surfaces 26 and 28 of the valve body 14. The central aperture 30 defines an inner annular valve seat surface 34.

The valve body 14 further includes a first fitting portion 36 that projects radially from the external circumferential surface 38 of the valve body 14. The first fitting portion 36 is formed as an elongate cylinder, and has a distal threaded portion 40. A first flow passage 42 is formed axially through the first fitting portion 36, opening onto the valve seat surface 34 at an inlet port 44. The central axes of the first fitting portion 36 and the first flow passage 42 are aligned along an axis 46 that is perpendicular to the rotational axis 32. The first flow passage 42 enlarges proximate the distal tip of the first fitting portion 36, defining an enlarged passage portion 48 that receives one end of a length of tubing 50. The interior of the tubing 50 forms a continuation of the first flow passage 42, which terminates at an outlet port 52 at the distal end of the tubing 50. A lock nut 54 is threaded onto the threaded portion 40 of the first fitting portion 36 of the valve body 14.

The valve rotor 16 includes a cylindrical head portion 56 that has approximately the same diameter as the disk portion 24 of the valve body 14. The head portion 56 of the valve rotor 16 defines an outer circumferential surface 58 and a circular inner end surface 60. The valve rotor 16 further includes a stem portion 62 that projects outwardly along the longitudinal axis of the head portion 56 from the center of the end surface 60. The stem portion 62 is formed as an elongate cylinder that has a diameter slightly larger (by 0.015 inches, for example) than the diameter of the central aperture 30 formed through the valve body 14, and a length greater than the distance between the first bearing surface 26 and second bearing surface 28 of the disk portion 24 of the valve body.

A second flow passage 64 is formed axially through the stem portion 62 and part way into the head portion 56 of the valve rotor 16. The longitudinal axis of the stem portion 62, and thus of the second flow passage 64, aligns with the pivot axis 32 when the valve rotor 16 is assembled with the valve body 14, as shall be discussed subsequently.

A radial flow passage 66 is formed transversely into the stem portion 62, opening into and intersecting the second flow passage 64. The radial flow passage 66 defines an outlet port 68 on an annular valve sealing surface 70 defined by the exterior of the stem portion 62. A pin 72 is inserted into the second flow passage 64 through the distal end of the stem portion 62, filling and thereby blocking the second flow passage 64 between the distal end of the stem portion 62 and the radial flow passage 66. The radial flow passage 66 thus serves as an extension of the second flow passage 64.

A radial fitting passage 73 is formed in the circumferential outer surface 58 of the head portion 56 of the valve rotor 16, and opens into and intersects the second flow passage 64. The collar fitting 18 is configured as a length of tubing that has one end formed to define a series of annular flanges 74. The flanged end of the collar fitting 18 is press-fit into the radial fitting passage 73 to secure the collar fitting 18 to the valve rotor 16. The interior of the tubular collar fitting 18 thus acts as an extension of the second flow passage 64. The radial outermost end of the inserted collar fitting 18 defines an inlet port 76.

Referring to FIGS. 2 and 3, the valve 10 is assembled by press-fit inserting the stem portion 62 of the valve rotor 16 through the central aperture 30 of the valve body 14. Because of the interference caused by the diameter of the stem portion 62 being larger than the central aperture 30, a liquid and gas tight seal is formed between the valve sealing surface 70 of the stem portion 62 and the valve seat surface 34 of the valve body 14. The valve rotor 16 is preferably formed from polytetrafluoroethylene (PTFE) or another malleable material to enable this press-fit seal while still permitting the valve rotor 16 to rotate.

The projecting end portion of the stem portion 62 is inserted into a retaining aperture 78 formed in one face of a cylindrical cap 80. The retaining aperture 78 is preferably tapered to enlarge in diameter toward the bottom of the aperture. At the bottom, the diameter of the aperture is substantially the same as the diameter of the stem portion 62 of the valve rotor 16, while at the entry to the aperture 78 its diameter is smaller than the diameter of the stem portion 62. The stem portion 62 is thus also press-fit into the cap 80.

When so assembled, the valve rotor 16 and cap 80 rotate as an assembly relative to the valve body 14. Because of the interference fit between the valve rotor 16 and valve body 14, there is some resistance that must be overcome for rotation. While the valve rotor 16 has been described as being preferably manufactured from PTFE, other machinable and moldable engineering thermoplastics and metals may be utilized. However, all materials defining the first flow passage 42 and second flow passage 64 should be inert to the organic solvents conventionally used for the type of chemical analysis or other application for which the valve 10 is to be employed. Also, in order to assure a seal and allow an interference fit, one or the other of the valve body 14 and valve rotor 16 should be softer relative to the other.

When PTFE is used for the valve rotor 16, suitable materials for the valve body are more rigid thermoplastics or metals, such as polyphenylene sulfide (PPS). The collar fitting 18, cap 80 and nut 54 are also preferably formed from strong, rigid thermoplastics, such as PPS for the collar fitting and acetal for the cap 80 and nut 54. The tubing 50 is preferably formed from stainless steel. However, the materials disclosed as being suitable for manufacture of the components of the valve 10 are provided by way of example only, and other materials would be suitable as can be readily determined by one of ordinary skill in the art. Additionally, it is possible that some of the individual components can be molded or machined as integral pieces. For example, the collar fitting 18 and valve rotor 16 can be formed as an integral one piece unit, and the valve body 14 and tubing 50 can also be integrally formed as a one piece unit.

Referring again to FIG. 1, the degree of rotation of the valve rotor 16 relative to the valve body 14 is limited by a stop pin 82. One end of the stop pin 82 is press-fit into an aperture 84 formed in the second bearing surface 28 of the disk portion 24 of the valve body 14. When so installed, the opposite end of the pin 82 protrudes orthogonally from the second bearing surface 28. The protruding end of the pin 82 is slidably received within an arcuate groove 86 formed in the end surface 60 of the head portion 56 of the valve rotor 16. The valve rotor 16 is thus constrained to rotate only to the extent of travel permitted by engagement of the pin 82 within the groove 86. In the preferred embodiment, the degree of movement permitted by this constraint is approximately 45°.

Referring to FIG. 2, when the valve rotor 16 is rotated fully in a first direction, as shown, the outlet port 68 of the second flow passage 64 in the valve rotor 16 is aligned in fluid flow communication with the inlet port 44 of the first flow passage 42 in the valve body 14. In this "on" position, liquid can flow from the inlet port 76 of the collar fitting 18 of the valve rotor 16 through the valve, exiting the outlet port 52 of the tubing 50 of the valve body 14.

Referring to FIG. 2, when the valve rotor 16 is rotated from this "on" position about the pivot axis 32 (FIG. 3), the arcuate groove 86 moves along the stop pin 82. As the valve rotor 16 is rotated, the outlet port 68 of the valve rotor 16 comes out of the alignment with the inlet port 44 of the valve body 14, blocking fluid flow through the valve 10. When the arcuate groove 86 has traveled fully, with the stop pin 82 contacting the opposite end of the arcuate groove 86, the valve rotor 16 has traveled approximately 45°, greater than the distance required to merely block fluid flow. This fully "off" position is indicated in phantom in FIG. 2 by collar fitting 18'.

To install the valve 10, the threaded portion 40 of the first fitting portion 36 of the valve body 14 is threaded into the inlet 88 of the HPLC instrument 12. The valve body 14 is twisted to thread the threaded portion 40 until the tubing 50 is fully inserted into a corresponding threaded recess in the inlet 88. When fully installed, the valve body 14 is adjusted so that the collar fitting 18 projects upwardly at an approximate angle of about 40°–45°, and preferably 40°, above horizontal when the valve rotor 16 is in the "on" position, as shown in FIG. 1. Conversely, when the valve rotor 16 is moved to the "off" position, the collar fitting 18 projects downwardly of horizontal, by approximately greater than zero to 5°, and preferably 5°, as shown in phantom by collar fitting 18' in FIG. 1. The nut 54 (FIGS. 2 and 3) is then rotated on the threaded portion 40 until tight against the inlet 88 of the HPLC instrument 12 to lock the valve 10 orientation, preventing the valve body 14 from easily rotating out of this disposition.

The collar fitting 18 on the valve rotor 16 is dimensioned to engage with a standard syringe connector, such as a Luer™ syringe connector. As shown in FIG. 1, the distal end fitting 20 of the syringe 22 has an annular inner sleeve 90 and an outer coaxial sleeve 92. When the syringe 22 is connected to the collar fitting 18, the inner sleeve 90 is received within the collar 18 and the outer sleeve 92 passes over the outside of the collar fitting 18. The internal diameter of the collar fitting 18 is preferably tapered slightly towards the center of the valve rotor 16, so as to correspond to the taper of the inner sleeve 90 of conventional syringe fittings.

This coupling makes a liquid tight seal between the syringe fitting 20 and the collar fitting 18, and also structurally connects the two so that the syringe 22 can be used as a lever handle to rotate the valve rotor 16. As shown in FIG. 1, the syringe 22 projects radially relative to the axis of rotation 32 of the valve rotor 16 when so installed.

Still referring to FIG. 1, the method for priming the pump of the HPLC instrument 12 using the valve 10 begins with the valve rotor 16 rotated to the "off" position, in which the collar fitting 18 projects angularly and downwardly. The syringe 22 is loaded with the liquid to be introduced into the HPLC instrument 12, and the syringe fitting 20 is engaged with the collar fitting 18 on the valve 10. The syringe 22 is then pushed or displaced upwardly, revolving about the axis of rotation 32, until the valve rotor 16 is in the "on" position. At this point, the collar fitting 18 and syringe 22 project upwardly at an angle. The plunger 94 of the syringe can then be withdrawn to draw out any air, as well as a small portion of liquid, from the pump of the HPLC instrument 12 and the valve 10. Once the withdrawn air or other gas enters the syringe 22, it rises to the upper end of the syringe 22 because of the syringe's upwardly angled disposition. The plunger 94 is then depressed to the extent required to introduce the desired quantity of liquid from the syringe 22, through the valve 10, into the pump of the HPLC instrument 12. The plunger 94 is not fully depressed, however, so that the withdrawn air is retained within the syringe 22. Once injection of the liquid is complete, the syringe 22 is pushed downwardly, rotating the valve rotor 16 to the "off" position. The syringe 22 can then be detached, with the priming operation complete and without any air having been introduced into the system.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A valve for use in controlling fluid flow between an inlet of an analytical instrument and a syringe, the valve comprising:

a valve body including a first fitting portion that can be coupled to the analytical instrument inlet, the valve body defining a cylindrical valve seat surface and a first passage extending from an inlet port opening onto the valve seat surface to an outlet port opening through a distal end of the first fitting portion; and a valve rotor including an engagement portion for rotatably engaging with the valve body and a second fitting portion, the engagement portion defining a cylindrical valve sealing surface that mates with the cylindrical valve seat surface of the valve body in a male-female arrangement, the second fitting portion projecting radially from the valve rotor, the valve rotor further defining a second passage extending from an inlet port defined by the second fitting portion to an outlet port opening onto the cylindrical valve sealing surface, the second fitting portion of the valve rotor sized to engage a distal fitting of a syringe, the syringe acting as a lever for rotation of the valve rotor when the syringe is engaged with the valve rotor to rotate the valve rotor about an axis of rotation between an off position, in which the outlet port of the valve rotor is nonaligned with the inlet port of the valve body to prevent fluid flow through the valve, and an on position, in which the outlet port of the valve rotor is aligned with the inlet port of the valve body to permit fluid flow from the syringe through the valve to the instrument inlet.

2. The valve of claim 1, wherein the first fitting portion of the valve body includes means for securing the valve relative to the instrument and wherein the second fitting portion of the valve rotor, and the syringe connected thereto, depend downwardly from horizontal when the valve rotor is in the off position, and depend upwardly from horizontal when the valve rotor is in the on position.

3. The valve of claim 1, wherein the valve body can be coupled to the instrument inlet such that the second fitting portion of the valve rotor, and the syringe engaged thereto, depend downwardly of horizontal when the valve rotor is in the off position, and depend upwardly of horizontal when the valve rotor is in the on position.

4. The valve of claim 1, wherein the second fitting portion of the valve rotor comprises an annular collar that is receivable between coaxial annular flanges defined by the distal fitting of the syringe.

5. The valve of claim 1, wherein the valve body includes an aperture defining the valve seat surface, and the engagement portion of the valve rotor comprises a stem defining the valve sealing surface, the stem of the valve rotor being received within the aperture of the valve body.

6. The valve of claim 5, wherein the stem of the valve rotor projects through the aperture on the valve body and is retained by a cap member.

7. The valve of claim 6, wherein the valve body defines first and second parallel bearing surfaces, the second fitting portion of the valve rotor bearing on the first bearing surface and the cap bearing on the second bearing surface.

8. The valve of claim 7, wherein the valve further comprises means for limiting rotation of the valve rotor to rotation between the on and off positions.

9. The valve of claim 8, wherein the means for limiting rotation of the valve rotor comprises a pin projecting from the valve body that is received within a groove defined in the valve rotor.

10. A valve for use in controlling fluid flow between an inlet of an analytical instrument and a syringe, the valve comprising:

a valve body including a first fitting portion for coupling to an inlet of an analytical instrument, the valve body defining a valve seat surface and a first passage extending from an inlet port opening onto the valve seat surface to an outlet port opening through a distal end of the first fitting portion; and a valve rotor including an engagement portion for rotatably engaging about an axis of rotation with the valve body and a second fitting portion projecting radially from the valve rotor relative to the axis of rotation, the engagement portion defining a valve sealing surface that mates with the valve seat surface of the valve body, the valve rotor further defining a second passage extending from an inlet port defined by the second fitting portion to an outlet port opening onto the valve sealing surface;

wherein the first passage of the valve body includes an inlet portion that terminates at the inlet port, the inlet portion of the first passage being aligned radially with respect to the axis of rotation of the valve rotor;

whereby a distal fitting of the syringe is engageable with the second fitting portion of the valve rotor to project radially from the engagement portion of the valve rotor to act as a lever for rotation of the valve rotor, the syringe being displaceable to rotate the valve rotor about the axis of rotation of the engagement portion between an off position, in which the outlet port of the valve rotor is nonaligned with the inlet port of the valve body to prevent fluid flow through the valve, and an on position, in which the outlet port of the valve rotor is aligned with the inlet port of the valve body to permit fluid flow from the syringe through the valve to the instrument inlet.

11. The valve of claim 10, wherein the valve seat surface of the valve body is cylindrical, and the valve sealing surface of the valve rotor is cylindrical.

12. The valve of claim 10, wherein the valve body and the valve rotor are connected in a male-female arrangement centered about the axis of rotation of the engagement portion of the valve rotor.

13. A valve for use in controlling fluid flow between an inlet of an analytical instrument and a syringe, the valve comprising:

a valve body including a disk portion defining a central aperture aligned on a longitudinal axis of the disk portion and a fitting portion projecting radially from the disk portion, the valve body further defining an outlet passage formed radially relative to the longitudinal axis of the disk portion and extending from the central aperture of the disk portion to a distal end of the fitting portion;

a valve rotor including a head portion and a stem portion, the head portion and stem portion being centrally aligned on a longitudinal axis of the valve rotor, the stem portion being rotatably received in sealing engagement within the central aperture of the valve body such that the longitudinal axis of the valve rotor is aligned with the longitudinal axis of the valve body, the valve rotor rotating within the valve body about the longitudinal axis of the valve rotor, the valve rotor defining:

a central passage extending along the longitudinal axis of the valve rotor from a proximal end within the head portion to a distal end adjacent the outlet passage of the valve body;

a first radial passage extending radially from the distal end of the central passage to an outer circumferential surface of the stem portion and capable of being aligned in fluid flow communication with the outlet passage of the valve body when the valve rotor is rotated to an on position, and of being disaligned with the outlet passage of the valve body when the valve rotor is rotated to an off position; and a second radial passage extending radially from the proximal end of the central passage to an outer surface of the head portion; and a tubular syringe fitting secured to the head portion of the valve rotor in axial fluid flow alignment with the second radial passage of the valve rotor such that the syringe fitting projects radially from the valve rotor relative to the longitudinal axis of the valve rotor, and such that applying a tangential force to the tubular syringe fitting causes rotation of the valve rotor for movement between the on and off positions.

* * * * *

UNITED STATES PATENT AND TRADEMARK OFFICE
CERTIFICATE OF CORRECTION

PATENT NO.  : 5,616,300
DATED       : April 1, 1997
INVENTOR(S) : D.W. Ford et al.

It is certified that error appears in the above-indentified patent and that said Letters Patent is hereby corrected as shown below:

COLUMN     LINE

[56]   Refs. Cited     Insert the following references:
       (U.S. Patent    5,178,186   1/1993    Levasseur     137/556
       Documents)      5,144,984   9/1992    Westerberg    137/625.18
                       4,388,272   6/1983    Gesteland     422/102
                       4,967,797   11/1990   Manska        137/625.47
                       4,393,726   7/1983    Tamm et al.   73/864.84
                       5,129,584   7/1992    Ridenour      239/579--

Signed and Sealed this

Twelfth Day of August, 1997

*Attest:*

BRUCE LEHMAN

*Attesting Officer*        Commissioner of Patents and Trademarks